US00PP19921P2

(12) United States Plant Patent
Korlipara

(10) Patent No.: US PP19,921 P2
(45) Date of Patent: Apr. 14, 2009

(54) ***HEDYCHIUM* PLANT NAMED 'TAHITIAN FLAME'**

(50) Latin Name: *Hedychium spp.*
Varietal Denomination: Doctor Moy

(75) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 11/986,114

(22) Filed: Nov. 19, 2007

(51) Int. Cl.
*A01H 5/00* (2006.01)

(52) U.S. Cl. ..... Plt./373

(58) Field of Classification Search ..... Plt./373, Plt./263.1
See application file for complete search history.

(56) References Cited

PUBLICATIONS http://web.archive.org/web/20061110114209/http:/www-.terranovanurseries.com/wholesale/modules.php?name=Content&pa=sh owpage&pid=113.*

* cited by examiner

*Primary Examiner*—Annette H Para
*Assistant Examiner*—S. B McCormick Ewoldt
(74) *Attorney, Agent, or Firm*—Klarquist Sparkman, LLP

(57) ABSTRACT

A new and distinct cultivar of *Hedychium* plant characterized by striking, strongly variegated leaves, showy fragrant flowers, repeat blooming, and excellent vigor.

2 Drawing Sheets

Botanical denomination: *Hedychium* spp.
Variety designation: 'Tahitian Flame'.
Parentage: *Hedychium* (*flavum*×*coccineum*), 'Doctor Moy'.

BACKGROUND OF THE INVENTION

The present invention relates to a new and distinct cultivar of an herbaceous perennial of the genus, *Hedychium,* and known by the cultivar name of 'Tahitian Flame'. The genus *Hedychium* is a member of the family *Zingiberaceae.* This cultivar occurred as natural branch mutation of *Hedychium* 'Doctor Moy' (an unpatented plant) in a greenhouse in Canby, Oreg. *Hedychium* 'Doctor Moy' was bred by retired plant breeder Dr. Moy and is an interspecific hybrid between *Hedychium. flavum* and *Hedychium. coccineum.* The new cultivar differs from its parent in having stronger variegation.

SUMMARY OF THE INVENTION

This new cultivar is unique due to its strong, striking, streaked variegation. This variegation is a great improvement over the parent, *Hedychium* 'Doctor Moy', as the streaking is much wider and brighter. In addition this new cultivar has showy fragrant flowers, repeat blooming, and excellent vigor.

This new cultivar has been reproduced only by asexual propagation (division and tissue culture). Each of the progeny exhibits identical characteristics to the parent plant. Asexual propagation by tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

FIG. 2 shows a close up with the flower.

FIG. 3 shows a leaf of *Hedychium* 'Tahitian Flame' on the right compared to *Hedychium* 'Doctor Moy', on the left.

DETAILED PLANT DESCRIPTION

Figure 1:
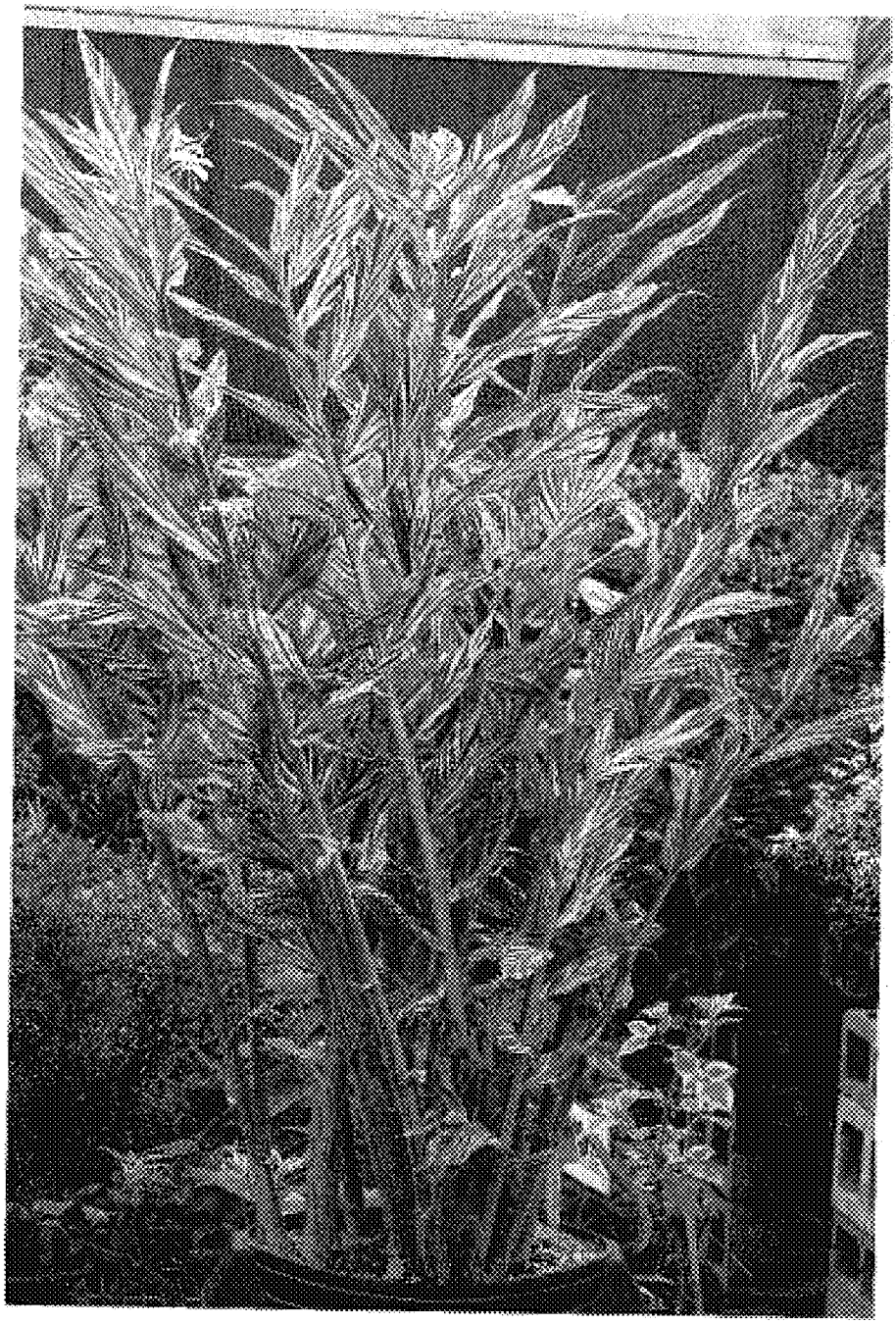
FIG. 1 shows a four-year-old *Hedychium* 'Tahitian Flame' growing in a five gallon container in the warm greenhouse in October in Canby, Oreg.

The following is a detailed description of the new cultivar based on observations of four-year-old specimens in October 2007 grown in five gallon containers in a warm greenhouse in Canby, Oreg. This greenhouse is kept at 62 to 65 degrees F. minimum and 95 degrees F. highs. The color descriptions are all based on the Royal Horticultural Society Colour Chart.

Plant:
- *Type.*—Herbaceous perennial, rhizomatous.
- *Form.*—Upright.
- *Hardiness.*—USDA Zones 7 (if given winter mulch) to 11.
- *Size.*—120 cm tall and 90 cm wide.
- *Habit.*—Clumping.
- *Pseudostem.*—Erect, reed-like; 15 mm wide and 60 to 120 cm long; leaf spacing 5 to 7 cm; glabrous; Green 138A to 138B, with narrow (1 mm to 2.5 mm wide), creamy white longitudinal stripes (Yellow Green 145D to Yellow White 158D).

Leaf:
- *Type.*—Simple.
- *Arrangement.*—Alternate, 2 ranked.

*Shape.*—Oblong lanceolate.
*Venation.*—Penni-parallel.
*Margins.*—Entire, somewhat revolute.
*Apex.*—Attenuate.
*Base.*—Clasping sheaths with scarious stipules.
*Size.*—19 cm to 28 cm long and 4 cm to 5.5 cm wide.
*Surface.*—Glabrous on both sides, leathery.
*Leaf color.*—Leaves topside deep green (Green 138A), with lighter green areas, Green 138A and Yellow Green 144A, and with varying widths of creamy white stripes (from 0.5 mm to areas of 15 mm wide), between Yellow 2D to 4C; main vein Green 138B; bottom side Green 138B to 138D with Yellow 4D where lighter on top. Inflorescence, flower bud, and flowers are identical to the mother plant, *Hedychium* 'Doctor Moy'.

Inflorescence:
*Type.*—Terminal dense spike with 2 to 4 flowers per bract.
*Size.*—11 cm wide and 15 cm deep.
*Bracts surrounding flowers.*—2.6 cm long and 2.1 cm wide, Green 146A widely and narrowly striped Yellow 4D.
*Bloom time.*—October to December in Canby, Oreg.
*Lastingness.*—Each spike lasts for 6 to 8 weeks in the greenhouse in Canby, Oreg.

Flower bud:
*Size.*—6.3 cm deep and 6 mm wide.
*Description.*—Slender, pointed, imbricate.
*Color.*—Orange, Yellow Orange 22B where exposed.

Flower:
*Type.*—Zygomorphic.
*Size.*—7.5 cm deep without pistil and 5.5 cm wide.
*Color.*—Yellow Orange 19C with a darker eye, Yellow Orange 21A.
*Petals.*—3, two lateral, each 3.4 cm long and 1.4 cm wide, oblanceolate, and one obliquely parted lip, 3.2 cm long and 2.3 cm wide.
*Calyx.*—Surrounds tube 2.5 cm deep and 3 mm wide, Yellow Green 145C.
*Staminodes.*—3, 3 cm long and 1.5 mm wide, Yellow Orange 22A.
*Pistil.*—1, 9.3 cm long, style is very slender, 4.7 cm long and Yellow Orange 19B, stigma is Yellow Green 146A.
*Filament.*—1, 4.6 cm long, wraps around style and Greyed Orange 167A.
*Anthers.*—10 mm long and Orange 28B.
*Pollen.*—Very little, Orange 28D.
*Fragrance.*—Strong and pleasant.

Fruit and seed: None. Plant is sterile and does not produce fruit or seed.

Pests and diseases: Spider mites, aphids, root rot, and leaf spots may occur. This plant has no know resistances.

Comparison to *Hedychium* 'Doctor Moy'

*Hedychium* 'Doctor Moy' (unpatented) is admired for its repeat blooming, long lasting blooms, showy flowers, its upright, non-falling habit, its sweet fragrance, and its unique variegation. Dr. Ying Doon Moy describes his plant as "Medium height plant has a large strong stem (peudostem), the distance between the leaves on the psuedostems are shorter, so the leaves of this variety has density. It has a special character in its shorter but broader leaves that is the green leaves having some light yellow stripes or spots in it. The orange flowers are fragrant and lovely."

*Hedychium* 'Tahitian Flame' has all these characteristics and much stronger, wider, and brighter variegation.

I claim:

1. A new and distinct cultivar of *Hedychium* plant as herein illustrated and described.

* * * * *

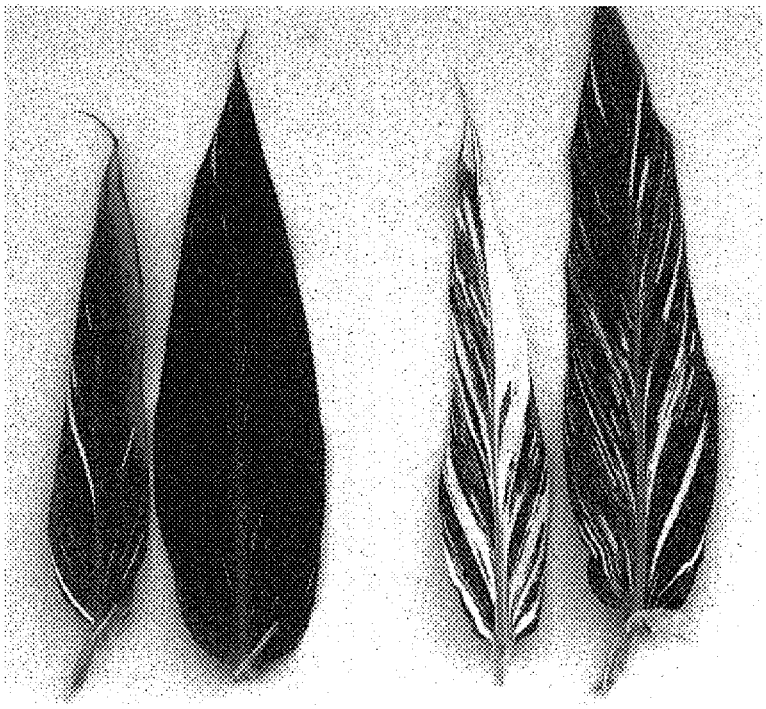

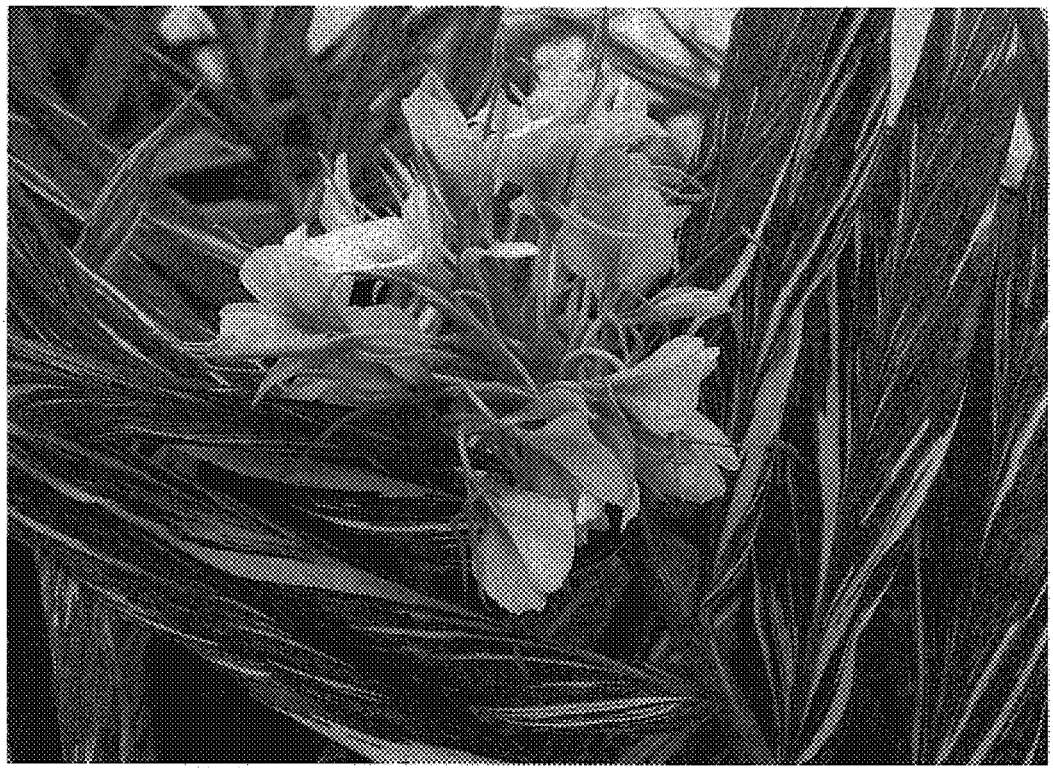
Figure 2 above, figure 3 below.